(12) United States Patent
Broughton et al.

(10) Patent No.: US 8,535,654 B2
(45) Date of Patent: Sep. 17, 2013

(54) DISINFECTING AND DETOXIFYING META-ARAMID PARTICLES

(75) Inventors: Roy M. Broughton, Opelika, AL (US); Hasan Basri Kocer, Bursa (TR); Shelby Davis Worley, Auburn, AL (US); Annelese Felmy Maddox, Newtown, PA (US); Wei Liu, Schaumburg, IL (US)

(73) Assignee: Auburn University, Auburn, AL (US)

( * ) Notice: Subject to any disclaimer, the term of this patent is extended or adjusted under 35 U.S.C. 154(b) by 0 days.

(21) Appl. No.: 12/875,562

(22) Filed: Sep. 3, 2010

(65) Prior Publication Data
US 2011/0250162 A1 Oct. 13, 2011

Related U.S. Application Data

(60) Provisional application No. 61/240,061, filed on Sep. 4, 2009.

(51) Int. Cl.
- *A61K 9/14* (2006.01)
- *A61K 8/88* (2006.01)
- *D06L 3/06* (2006.01)
- *C02F 1/76* (2006.01)

(52) U.S. Cl.
CPC ... *A61K 8/88* (2013.01); *A61K 9/14* (2013.01); *C02F 1/76* (2013.01); *D06L 3/06* (2013.01); *Y10S 2/901* (2013.01); *Y10S 8/925* (2013.01)
USPC ............... 424/78.17; 2/901; 8/531; 8/925; 424/404; 424/489

(58) Field of Classification Search
None
See application file for complete search history.

(56) References Cited

U.S. PATENT DOCUMENTS

| 3,287,324 | A | 11/1966 | Sweeny |
| 5,093,431 | A | 3/1992 | Raynor |
| 5,490,983 | A | 2/1996 | Worley et al. |
| 5,882,357 | A | 3/1999 | Sun et al. |
| 6,548,054 | B2 | 4/2003 | Worley et al. |

(Continued)

FOREIGN PATENT DOCUMENTS

WO 2006099567 9/2006

OTHER PUBLICATIONS

J Lee, RM Broughton, SD Worley, TS Huang. "Antimicrobial Polymeric Materials; Cellulose and m-Aramid Composite Fibers." Journal of Engineered Fibers and Fabrics, vol. 2, Issue 4, 2007, pp. 25-32.*

(Continued)

*Primary Examiner* — Brian Gulledge
*Assistant Examiner* — Isaac Shomer
(74) *Attorney, Agent, or Firm* — Gardner Groff Greenwald & Villanueva, PC

(57) ABSTRACT

Porous, permeable particles of meta-aramid can be chlorinated or brominated to produce antimicrobial and detoxifying particles for use in applications such as, but not limited to, nonwoven webs, paper, textiles, absorbent articles, healthcare products, paints, filter materials, powder coatings, clear coatings, molded plastic articles, binders for fibrous materials, and the like. The particles can be charged with halogen before or after incorporation into the application medium. The particles can contain blends of meta-aramid with other polymers such as, but not limited to, cellulose, cellulose acetate, polyurethane, and the like. The particles will be effective at inactivation of pathogenic and odor-causing microorganisms and toxic chemical agents. The particles, which contain N-halamine units, have unexpected resistance to ultraviolet light degradation.

33 Claims, 1 Drawing Sheet

(56) References Cited

U.S. PATENT DOCUMENTS

| | | | |
|---|---|---|---|
| 6,969,769 | B2 | 11/2005 | Worley et al. |
| 7,335,373 | B2 | 2/2008 | Worley et al. |
| 7,687,072 | B2 | 3/2010 | Worley et al. |
| 2003/0144638 | A1 | 7/2003 | Quincy, III |
| 2004/0086480 | A1* | 5/2004 | Worley et al. .............. 424/78.22 |

OTHER PUBLICATIONS

H Farkas-Himsley. "Killing of Chlorine-Resistant Bacteria by Chlorine-Bromine Solutions." Applied Microbiology, vol. 12, No. 1, Jan. 1964, pp. 1-6.*

J Lee. "Synthesis and Applications of Novel Antimicrobial Polymeric Materials." PhD Thesis, Auburn University. Aug. 7, 2006. pp. i-xviii and 1-122.*

Barnes et al.; Modification of Silica Gel, Cellulose, and Polyurethane with a Sterically Hindered N-Halamine Moiety to Produce Antimicrobial Activity; Journal of Applied Polymer Science; vol. 105, pp. 2306-2313 (2007).

Kim et al.; Antimicrobial Polyethylene Terephthalate (PET) Treated with an Aromatic N-Halamine Precursor, m-Aramid; Journal of Applied Polymer Science; vol. 114, pp. 3835-3840 (2009).

Lee et al.; Antimicrobial Fibers Created via Polycarboxylic Acid Durable Press Finishing; Textile Research Journal; vol. 77, pp. 604-611 (2007).

Lee et al.; Antimicrobial Polymeric Materials; Cellulose and m-Aramid Composite Fibers; Journal of Engineered Fibers and Fabrics; vol. 2, Issue 4, pp. 25-32 (2007).

Lee et al; Preparation and Application of an s-Triazine-Based Novel N-Halamine Biocide for Antimicrobial Fibers; Fibers and Polymers; vol. 8, No. 2, pp. 148-154 (2007).

Liang et al.; N-halamine biocidal coatings; J Ind Microbiol Biotechnol; vol. 34, pp. 157-163 (2007).

Lin et al.; Antimicrobial Treatment of Nylon; Journal of Applied Polymer Science; vol. 81, pp. 943-947 (2001).

Lin et al.; Biocidal Polyester; Journal of Applied Polymer Science; vol. 85, pp. 177-182 (2002).

Ren et al.; Antimicrobial coating of an N-halamine biocidal monomer on cotton fibers via admicellar polymerization; Colloids and Surfaces, A: Physicochem. Eng. Aspects; vol. 317; pp. 711-716 (2008).

Salter, et al.; N-chloramide modified Nomex as a regenerable self-decontaminating material for protection against chemical warfare agents; J. Mater, Sci., vol. 44, pp. 2069-2078 (2009).

Sandstrom et al.; Biocidal Aramide Fabrics for Emergency Responders: Formation and Properties of Aramide Halamine; Textile Research Journal, vol. 77, pp. 591-596 (2007).

Sun et al.; Novel Refreshable N-Halamine Polymeric Biocides Containing Imidazolidin-4-one Derivatives; Journal of Polymer Science: Part A: Polymer Chemistry; vol. 39, pp. 3073-3084 (2001).

Sun et al.; Novel Refreshable N-Halamine Polymeric Biocides: N-Chlorination of Aromatic Polyamides; Ind. Eng. Chem. Res., vol. 43, pp. 5015-5020 (2004).

Termonia, Yves; Monte Carlo Diffusion Model of Polymer Coagulation; Physical Review Letters, vol. 72, No. 23, pp. 3678-3681 (1994).

Worley et al.; Novel N-halamine siloxane monomers and polymers for preparing biocidal coatings; Surf Coat Int Part B: Coat Trans., vol. 88, pp. 93-100 (2005).

* cited by examiner

DISINFECTING AND DETOXIFYING META-ARAMID PARTICLES

CROSS REFERENCE TO RELATED APPLICATIONS

This application claims priority to U.S. Provisional Application Ser. No. 61/240,061, filed Sep. 4, 2009, hereby incorporated by reference in its entirety for all of its teachings.

ACKNOWLEDGEMENTS

This invention was made with government support under Grant FA8650-07-1-5908 awarded by the United States Air Force. The government has certain rights in the invention.

BACKGROUND

A class of compounds termed N-halamines has been shown to provide excellent antimicrobial properties, particularly for polymers and coatings containing these functional groups. These compounds possess the advantage that their precursors can be chlorinated or brominated in situ to produce biocidal activity and be rehalogenated when the oxidative halogen on the compounds has been exhausted. For example, poly-styrene derivatized with N-chlorinated or N-brominated hydantoinyl functional groups can be used to disinfect potable water (see U.S. Pat. Nos. 5,490,983, 6,548,054 B2, 7,687,072 B2) and, as a matter of fact, is currently being used for water disinfection by low-income families in developing nations such as India. The N-halamine polymer technology can further be applied to produce antimicrobial coatings on surfaces such as textiles (see for example, U.S. Pat. Nos. 6,969,769 B2, 7,335,373 B2, 5,882,357). It has recently been demonstrated that the N-chlorinated hydantoinyl siloxane polymer addressed in U.S. Pat. No. 6,969,769 B2 can also be used in detoxification of chemical agents (Salter, et al., *J. Mater. Sci.*, 44, 2069 (2009)). Any N-halamine coating will be antimicrobial and capable of detoxification since the bound halogen is oxidative upon transfer to receptor sites. Heretofore, two limitations of N-halamine polymer coatings have been their oxidative halogen loading capacities (less than 1% by weight chlorine) and their lack of resistance to ultraviolet photodegradation. Thus, it would be desirable to create an N-halamine polymer coating which could load a higher weight percentage of halogen, so as to increase its biocidal and detoxification efficacies (lower contact times necessary for complete inactivations of pathogens and toxic chemical agents) and which could resist ultraviolet photodegradation in sunlight.

Meta-aramid (poly-m-phenylene isophthalamide), generally sold under the trade name Nomex™, is known to be an excellent fire-resistant polymer. It can be prepared by reaction of isophthaloyl chloride with m-phenylene diamine in a solvent such as tetrahydrofuran (see for example U.S. Pat. No. 3,287,324). It is used in commerce in the form of a fiber or film. It contains an acyclic amide nitrogen atom which can be halogenated by exposure to aqueous free chlorine or bromine (see chemical structure below). It has been shown that Nomex fibers achieve

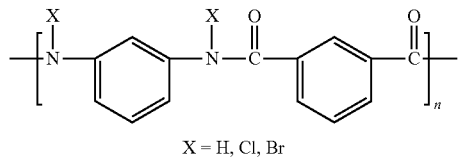

X = H, Cl, Br chlorination with aqueous household bleach with much less decomposition than does its isomer p-aramid, trade name Kevlar, (see Sun and Sun, *Ind. Eng. Chem. Res.*, 43, 5015 (2004)); however, a maximum concentration of only about 0.1 weight percent of oxidative chlorine (expressed as wt % $Cl^+$) could be loaded onto the Nomex fibers in that work. This loading demonstrated antibacterial activity for the fibers, but the loading decreased substantially over time and under washing conditions, and only 0.1 wt % chlorine would not be able to provide sustained biocidal activity. Sandstrom and Sun extended the Nomex fiber work to a study of thermal and UV stability for chlorinated Nomex in firefighter uniforms (Sandstrom and Sun, *RJTA*, 10, 13 (2006); Sandstrom et al., *Tex. Res. J.*, 77, 591 (2007)). Again the fibers contained very low chlorine loadings (less than 0.1 wt %), but the authors noted some UV stability over a one hour irradiation period as long as the fibers were maintained in a very dry state. Under controlled humidity tests in a weathering chamber the chlorinated fibers were not thermally or photolytically stable. It has also been shown that the loading of chlorine can be increased for fibers containing a blend of Nomex polymer and cellulose up to almost 1 wt % if Nomex and cellulose are dissolved in an ionic liquid solvent and co-extruded into fibers (see Lee et al., *J. Eng. Fib. Fab.*, 2, 25 (2007)). Upon chlorination, the fibers became bactericidal. However, when the Nomex polymer content in the blended fibers was above 10 weight percent, the tenacities of the fibers were dramatically decreased rendering them impractical for commercial use. A similar study has been recently reported for a Nomex-coated/polyethylene terephthalate prepared by applying a dimethylacetamide solution of Nomex to PET fabric using a pad-dry-curing process (Kim et al., *J. Appl. Polym. Sci.*, 114, 3835 (2009)). The treated Nomex/PET was antibacterial but only could load about 0.4 wt % chlorine which again would not provide sustained antimicrobial activity. The detoxification study mentioned above (Salter, et al., *J. Mater. Sci.*, 44, 2069 (2009)) employed Nomex derivatized with the hydantoinyl siloxane of U.S. Pat. No. 6,969,769 B2. The chlorine loadings in that study were about 0.32 wt % which would be too low for sustained detoxification activity. In summary, loadings of more than 1 wt % chlorine on Nomex fibers or its co-polymer blends and sustainable UV stability under real-world conditions have not been obtained heretofore. The most probable reason for this is that the oxidative chlorine is not able to penetrate the surfaces of the fibers due to lack of porosity and low permeability of the chlorine into the polymer structure. Hence any antimicrobial or detoxification activity of the treated Nomex fibers will be short-lived due to rapid exhaustion of the bound oxidative chlorine on the surfaces of the fibers.

Thus, porous, permeable antimicrobial/detoxification particles of Nomex or its blends with other polymers such as cellulose, cellulose acetate, polyurethane, and the like, would be desirable because they should bind much more oxidative chlorine than do non-porous fibers which would enable extended antimicrobial and detoxification activity and possibly less photodegradation due to the fact that much of the halogen would be less accessible to the UV photons when buried within the pores than those halogens bound on the surface. The N-halamine polymeric biocide as an amorphous solid, which is the subject of U.S. Pat. No. 5,490,983, has been broadcast into nonwoven webs for use in personal care absorbent articles (see US Patent 2003/0144638 A1) and shown to work well for this application. The current invention which involves Nomex particles and its blends should work well in similar applications for providing antimicrobial activity as well as in numerous other applications such as water and air filters, military textiles, health care textiles, paints, and other coatings. A byproduct of antimicrobial activity is the destruction of noxious odors in personal care absorbent articles, textiles, paint coatings in medical facilities, and the like. A distinct advantage of the treated Nomex and Nomex blend particles will be its lower cost relative to other biocidal particles such as that disclosed in U.S. Pat. No. 5,490,983 and 2003/0144638 A1.

Previous work on Nomex and Nomex blends relates to the materials existing as fibers, not porous particles.

SUMMARY OF THE INVENTION

The invention relates to porous microscopic particles of Nomex and its blends with other polymers such as, but not limited to, cellulose, cellulose acetate, polyurethane, and the like. A second aspect of the invention relates to halogenation of the amide nitrogen atoms of the Nomex moieties in porous particle form so as to produce high weight percent loadings of covalently bound oxidative chlorine or bromine for the purpose of inactivating microorganisms and detoxifying chemical agents. A third aspect of the invention relates to substantially increasing the oxidative halogen loading of the Nomex and Nomex/polymer blends relative to previous work involving Nomex fibers. A fourth aspect of the invention relates to providing increased stability toward ultraviolet photodegradation for the halogenated Nomex and Nomex/polymer blends. A fifth aspect of the invention relates to the utility of the halogenated Nomex and Nomex/polymer blends in nonwoven webs, absorbent articles, textiles, health care products, paints, water and air filters, and the like.

The present invention relates to the preparation of the porous Nomex and Nomex/polymer blended particles and to the halogenation thereof with aqueous free chlorine or bromine. It also relates to the broadcasting of the particles into various matrices such as nonwovens, paints, paper, filters, and the like. Additional advantages will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Figure 1A:
FIG. 1A shows an untreated water filter with no particles present on the filter.

Before the present compounds, compositions, articles, devices, and/or methods are disclosed and described, it is to be understood that the aspects described below are not limited to specific preparation methods; specific preparation methods may vary. It is also to be understood that the terminology used herein is for the purpose of describing particular aspects only and is not intended to be limiting.

In this specification and in the claims which follow, reference will be made to a number of terms which shall be defined to have the following meanings:

It must be noted that, as used in the specification and the appended claims, the singular forms "a", "an", and "the" include plural referents unless the context clearly dictates otherwise. Thus, for example, reference to an "unhalogenated compound" can include two or more such compounds.

Ranges may be expressed as from "about" one particular value, and/or to "about" another particular value. When such a range is expressed, another aspect includes from the one particular value and/or to the other particular value. It will be further understood that the endpoints of each of the ranges are significant both in relation to the other endpoint, and independently of the other endpoint.

References in the specification and appended claims to weight percent (wt %) of a particular element or component in a composition or article, denote the weight relationship between the particular element or component and the total weight of the formulation or composition in which the element or component is included.

As used herein, the terms "antimicrobial" and "biocidal" means activity which inactivates or kills microorganisms.

As used herein, the terms "detoxify" or "detoxification" mean destruction of toxic chemical agents.

As used herein, the term "photodecomposition" means destruction of an element or component in a composition or article by exposure to ultraviolet (UV) photons.

As used herein, the term "Nomex" means the compound poly-m-phenylene isophthalamide, first registered by DuPont, Inc. as the fiber Nomex™. It is to be understood that the polymer poly-m-phenylene isophthalamide is easily synthesized in the laboratory and is available from several commercial sources under various trade names. For example, the term "Nomex" as used herein refers to the polymer structure below having the chemical name poly-m-phenelene isophthalamide, which can exist as fibers or films, or in a mixture with other polymers.

As used herein, the term "unhalogenated Nomex" means the structure below in which each X is H:

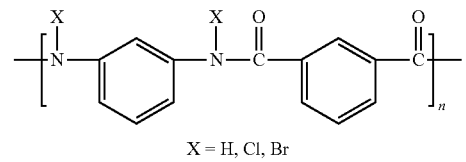

X = H, Cl, Br

As used herein, the term "halogenated Nomex" means the structure above in which at least one X is Cl or Br.

As used herein, the term "Nomex blend" means a blend of Nomex with any other polymer such as, for example, cellulose, cellulose acetate, polyurethane, and the like.

As used herein, the term "matrix" means material into which particles can be inserted such as nonwovens, textiles, paints, filters, absorbent articles, and the like.

As used herein, the term porous means a structure which allows permeation of halogen (e.g., halogenating agents) throughout the structure, whether by liquid flow into defined openings or pores, or by diffusion through the solid substance of the particle. Not wishing to be bound by theory, both porosity and permeability, or diffusion are likely mechanisms operative in the invention, and the term "porosity" or "porous" is intended to include both.

The present invention may be understood more readily by reference to the following detailed description of specific embodiments and the examples included therein.

Porous particles of Nomex can be produced by dissolving Nomex polymer (e.g., fibers or films) in an ionic liquid like 1-butyl-3-methylimidazolium chloride or an organic solvent such as DMF, followed by rapidly precipitating the dissolved Nomex in a stirred excess non-solvent (for the polymer) such as water or ethanol. Porous particles of Nomex blends can be produced by dissolving a mixture of Nomex polymer and other polymers such as, for example, cellulose, cellulose acetate, polyurethane, and the like in an ionic liquid like 1-butyl-3-methylimidazolium chloride or an organic solvent such as DMF followed by rapidly precipitating the dissolved Nomex blend in a stirred excess solvent such as water or ethanol dependent on the nature of the polymer. Ethanol could be used for cellulose or cellulose acetate. Small amounts of an inorganic salt such as lithium chloride are occasionally needed for complete dissolution when organic solvents are employed. A preferred weight percent of Nomex in the blend should be about 2 to 10. The Nomex blends can also contain superabsorbent polymers such as starch so as to absorb moisture which can enhance their biocidal and detoxification activities. In one aspect, the unhalogenated Nomex porous particles have a diameter from 0.5 μm to 10 μm. In another aspect, the particle diameter is 1 μm, 2 μm, 3 μm, 4 μm, 5 μm, 6 μm, 7 μm, 8 μm, 9 μm, or 10 μm, wherein any value can provide a lower and upper limit of the diameter range.

After producing the unhalogenated Nomex particles using the techniques described above, the unhalogenated Nomex particles can be halogenated by contacting the particles with a suitable halogenating agent. The degree of halogentation can vary depending upon reaction conditions, ranging from partial halogentation to complete halogentation of the unhalogenated Nomex particles. In one aspect, the porous Nomex particles or Nomex particle blends can be chlorinated by soaking the particles at ambient temperature in dilute aqueous solutions of about 10 wt % household bleach (sodium hypochlorite). The pH should be controlled in the range of 7 to 11, with pH 7 preferred for high chlorine loadings (greater than 6 wt % chlorine). Alternative chlorination sources such as calcium hypochlorite, chloroisocyanurates, dichlorohydantoins, and t-butyl hypochlorite, the latter if organic solvents are used, can be employed. In other aspects, bromination of the Nomex particles or Nomex particle blends can be achieved by soaking in aqueous bromine solution (see Example 7). Other bromination reagents which could be used include sodium or potassium bromide in the presence of an oxidizer such as potassium peroxy monosulfate and brominated hydantoins. Halogenation of the Nomex particles or Nomex particle blends can also be effected after the unhalogenated particles are broadcast into a matrix such as a nonwoven, textile, filter, paint, absorbent article, and the like. In one aspect, the halogenated Nomex porous particles have a diameter from 0.5 μm to 10 μm. In another aspect, the particle diameter is 1 μm, 2 μm, 3 μm, 4 μm, 5 μm, 6 μm, 7 μm, 8 μm, 9 μm, or 10 μm, wherein any value can provide a lower and upper limit of the diameter range. In another aspect, the halogen content of the particle is from 0.5% to 20% by weight of the particle. In another aspect, the halogen content of the particle is from 1%, 2%, 3%, 4%, 5%, 6%, 7%, 8%, 9%, 10%, 12%, 14%, 16%, 18, or 20% by weight of the particle. In a further aspect, the halogen content of the particle is from 2-fold, 3-fold, 4-fold, 5-fold, 10-fold, 20-fold, 30-fold, 40-fold, 50-fold, 75-fold, or 100-fold greater when compared to halogenating a commercial Nomex fiber.

Any of the particles and particle blends described herein can be incorporated into a matrix. For example, halogenated Nomex particles or particle blends can be biocidal and capable of detoxification of chemical agents. Since the great majority of the bound chlorine or bromine sites are contained within the pores of the particles, they also become resistant to photodecomposition. Since the weight percent halogen obtainable for the particles is much higher than that possible for Nomex fibers and Nomex fiber blends, the efficacy at disinfection and detoxification will be greater.

The particles can be broadcast into matrices or onto surfaces in a variety of ways including, but not limited to, soaking in solvents, followed by drying at elevated temperatures (up to 50° C. if already halogenated), blowing them into the matrix, or depositing them onto a surface.

One of skill in the art may determine alternative means of producing Nomex particles or Nomex particle blends and alternative means of broadcasting them into matrices.

The present invention is more particularly described in the following examples which are intended as illustrative only since numerous modifications and variations therein will be apparent to those skilled in the art.

EXAMPLES

The following examples are put forth so as to provide those of ordinary skill in the art with a complete disclosure and description of how the compounds, compositions, articles, devices, and/or methods described and claimed herein are prepared and evaluated, and are intended to be purely exemplary, and are not intended to limit the scope of what the inventors regard as their invention. There are numerous variations and combinations of preparation conditions, e.g. component concentrations, desired solvents, solvent mixtures, temperatures, pressures, and other preparation conditions that can be used to optimize the halogen loading obtained from the described process. Only reasonable and routine experimentation will be required to optimize such process conditions.

Example 1

Preparation of Unhalogenated and Chlorinated Porous Nomex Particles 50 grams of an ionic liquid, 1-buthyl-3-methyl-imidazolium chloride (Aldrich Chemicals Inc.) were added to a round bottom flask containing 0.62 gram of Nomex™ (DuPont, Corp.) fibers which were cut into small pieces to improve mixing. The solution was stirred with a mechanic stirrer at 80° C. for 72 hours until the fiber was completely dissolved. The solution was withdrawn with a syringe and precipitated in 200 mL of ethanol accompanied by vigorous agitation using a household blender. A uniform hazy suspension (ethanol, aramid, and ionic liquid) was produced. The cloudy suspension was filtered using a filter paper and then washed with distilled water and dried in air. The diameters of the resulting porous Nomex particles were between 1 and 2 μm.

The particles were then chlorinated using a commercial household hypochlorite bleach solution diluted 9/1 with tap water. The pH was adjusted to 7 using 6 N hydrochloric acid. The particles were placed in the solution for 1 hour at room temperature with mild stirring. The particles were then collected on filter paper, rinsed thoroughly with distilled water, and dried for 1 hour at 45° C. to remove any residual free chlorine.

The particles were analyzed for retained chlorine using a modified iodometric/thiosulfate titration procedure. In a 125 mL conical flask, 0.25 g of potassium iodide was dissolved in 10 mL of 0.1 N acetic acid and 90 mL of absolute ethanol. Weighed particles were added to the flask, and standardized 0.00375 N sodium thiosulfate solution was slowly added to the flask until reaching the endpoint (from yellow to colorless), and the solution remained colorless for 1 min. The amount of sodium thiosulfate solution consumed was recorded. The following equation was used to determine the weight percent Cl$^+$ loading on particles.

$$Cl^+ \text{ wt }\% = (N \times V \times 35.45)/(2 \times W) \times 100\%$$

where N and V are the normality (eqv/L) and volume (L), respectively, of the sodium thiosulfate consumed in the titration, and W is the weight of the samples in grams. The chlorine content of the chlorinated particles (Nomex-Cl) was measured as 6.72 wt %. The active chlorine loading of the particles was significantly higher compared to Nomex fibers as received, which was only 0.11 wt % at the same chlorination conditions.

Example 2

Preparation of Unhalogenated and Chlorinated Porous Nomex/Cellulose Particles

24 grams of an ionic liquid (1-buthyl-3-methyl-imidazolium chloride), were added to a flask containing 0.5 g Nomex™ aramid fibers which were cut into small pieces to improve mixing. They were stirred in a centrifugal mixer at 2500 rpm for about 20 minutes until the fiber was soaked by the ionic liquid. Then 0.5 grams of ground bleached cotton cellulose was added to the above solution, and mixing was continued for 1 hour. The solution was heated at 80° C. for 1 hour to lower the solution viscosity. Mixing and heating were repeated alternately to complete dissolution. The above solution was subsequently diluted by 3/1 with additional solvent.

The solution then was withdrawn with a syringe and injected into 200 mL of ethanol while undergoing vigorous agitation with a household blender. A uniform hazy suspension (ethanol, aramid, cellulose, and ionic liquid) was observed. Upon standing, a cloudy agglomeration began to settle from the suspension. Before complete agglomeration, the cloudy suspension was centrifuged, and the top clear solution was decanted. The collected aramid/cellulose sample was re-suspended in distilled water and centrifuged twice more, and then re-suspended in 180 mL of distilled water. Commercial household hypochlorite bleach (20 mL) was added, and the pH value was adjusted to 7 using 6 M hydrochloric acid. The chlorination solution was stirred at room temperature for 1 hour. The particles obtained were again centrifuged, washed at least 3 times with water, and then dried in a freeze dryer, followed by drying in air at 45° C. for 1 hour to remove any residual free chlorine.

The Nomex/cellulose porous particles obtained were analyzed for retained chlorine using a standard iodometric/thiosulfate titration procedure. The average chlorine content of the Nomex/cellulose particles was 4.31 wt % for four independent trials.

Example 3

Preparation of Unhalogenated and Chlorinated Permeable Nomex/Cellulose Blended Films from Particles

24 grams of an ionic liquid (1-butyl-3-methylimidazolium chloride) were added to a flask containing 0.5 gram of Nomex™ fibers which were cut into small pieces to improve mixing. The solution was stirred in a centrifugal mixer at 2500 rpm for about 20 minutes until the fiber was well dispersed. Then 0.5 gram of ground bleached cotton cellulose was added to the above solution, and mixing and heating to 80° C. were repeated alternately to complete dissolution. To lower the solution viscosity, it was diluted 3/1 with additional solvent.

The solution was withdrawn with a syringe and injected into 200 mL of ethanol during vigorous agitation effected by a household blender. A uniform hazy suspension (ethanol, aramid, cellulose, and ionic liquid) was produced. Upon standing, a cloudy agglomeration began to settle from the suspension. The cloudy suspension was stirred and filtered through a filter paper and allowed to dry in air. While wet, the particles could be re-suspended from the filter paper into water, but if allowed to dry, the particles adhered to each other on the filter paper and to the filter paper, forming a film. The film could be separated from the filter paper in small pieces.

The pieces of film were chlorinated using commercial household hypochlorite bleach diluted 9/1 with distilled water. Two bleach solutions were prepared, one adjusted to pH 9 with sodium bicarbonate, and a second adjusted to pH 7 using 6 N hydrochloric acid. Film samples were placed in each of the solutions for 1 hour at room temperature with mild stirring. The chlorinated film samples were collected on filter paper, rinsed thoroughly with distilled water, and dried for 1 hour at 45° C. to remove any residual free chlorine.

The samples were analyzed for retained chlorine using a standard iodometric/thiosulfate titration procedure. The chlorine contents of the blended film samples chlorinated at pH 7 and 9 were measured to be 6.08 wt % and 4.7 wt %, respectively. Thus higher chlorine loadings can be obtained at neutral pH, and much higher chlorine loadings can be obtained for porous Nomex/cellulose blended particles than for blended fibers. The adherence of the particles to each other and to paper upon drying suggests that they might adhere to a substrate matrix without binder if applied wet and then subsequently dried.

Example 4

Application of Porous Nomex Particles to a Commercial Filter Medium and Evaluation of its Antimicrobial Performance

Figure 1B:
FIG. 1B shows unchlorinated Nomex porous particles effectively captured in an embedded filter swatch.

0.06 gram of unchlorinated porous Nomex particles, as described in Example 1, were dispersed in 500 mL of distilled water, and the dispersion was filtered through a commercial water filter material (Argonide™, Argonide Corp.) (FIG. 1A), which weighed 1.14 grams and was 3 inches in diameter. The particles were effectively captured, and after drying were quite well trapped in the filter (FIG. 1B). The same procedure was used to prepare an embedded filter swatch with the chlorinated particles (Nomex-Cl, 6.72 wt % Cl$^+$) described in Example 1. The chlorine content of the chlorinated particle embedded filter swatch was measured as 0.29 wt % relative to the weight of the whole filter swatch.

Both Nomex and Nomex-Cl particle-embedded filters were subsequently evaluated for antibacterial effects. The treated filter swatches were challenged with *Escherichia coli* O157:117 (ATCC 43895) bacterial suspensions. 25 μl of the bacterial suspension were added to the center of a 1 inch square filter swatch, and a second identical swatch was laid on the first swatch held in place by a sterile weight. The contact times for the swatches with the bacteria were 15 and 30 minutes. At those contact times the filter swatches were quenched with 0.02 N sodium thiosulfate solution to remove any oxidative chlorine which could cause extended disinfection. Serial dilutions of the solutions contacting the surfaces were plated on Trypticase agar, incubated for 24 hours at 37° C., and colony counts were made to determine the presence of viable bacteria.

As shown in Table 1, the unchlorinated control samples, Nomex, provided 4.37 log reduction, due to the adhesion of bacteria to the filter swatches (wood-pulp), within a 30 minute contact time interval. In general, 4 log reductions for control samples are relatively high; however, nano alumina-grafted microglass fibers in the filter offer bacteria a high surface area for adhesion. The chlorinated filter samples, Nomex-Cl, showed excellent antimicrobial activity. All *E. coli* bacteria were inactivated by the treated swatches within the contact interval of 30 minutes. The inactivating rates of the chlorinated treated swatches are not sufficient for disinfection applications for flowing potable water; however, they would be sufficient for use in inactivating bacteria trapped in the filters over a period of time, thus making the filters safe for workers who eventually have to handle the filters.

TABLE 1

Biocidal activity of chlorinated Nomex-particle embedded filter.

| Sample | Contact time (min) | Total bacteria (Log) | Bacterial reduction (Log) |
|---|---|---|---|
| Inoculum |  | 7.10 |  |
| Nomex Filter (control) | 30 | 2.73 | 4.37 |
| Nomex-Cl Filter | 15 | 2.53 | 4.57 |
|  | 30 | 0 | 7.10 |

Example 5

Stability Toward Irradiation with Ultraviolet Photons

UV light stability of the bound chlorine on the porous Nomex particles was measured by using an Accelerated Weathering Tester (The Q-panel Company, Cleveland, Ohio, USA). The samples were placed in the UV (Type A, 315-400 nm) chamber for times in the range of 3 to 72 hours. After a specific time of exposure to UV irradiation, the samples were removed from the UV chamber and titrated, or rechlorinated and titrated. The temperature in the chamber was 37.6° C., and the relative humidity was 17% during the UVA light irradiation.

The UVA light stability of the N—Cl bond of the particles is summarized in Table 2. The chlorinated porous Nomex particles (Nomex-Cl) lost only 22 wt % of bound chlorine within 24 hours of UVA light exposure. In addition, almost all of the initial chlorine loading was provided upon rechlorination indicating little significant decomposition of the polymer itself in the presence of the UVA irradiation over the entire 24 hours of exposure. Porous Nomex-Cl particles were further investigated through UVA light exposure and rechlorination cycles. The chlorine loss was 37% within 72 hours of UVA light exposure indicating the presence of very stable N—Cl bonds, and/or the N—Cl bonds were protected from UVA exposure by the phenyl moieties or by their submersion in the pores of the particles. Consequently, the stability was quite remarkable given that a time period of exposure in the UV chamber was equivalent to the same time in direct midday summer sunlight.

TABLE 2

Stability toward UV light exposure of porous Nomex-Cl (Cl$^+$ wt % remaining) particles.

| Exposure Time | Cl$^+$ wt % | % Chlorine Loss |
|---|---|---|
| 0 | 6.79 |  |
| 3 hours | 6.32 | 7 |
| 24 hours | 5.33 | 22 |
| Rechlorination | 6.59 |  |
| 72 additional hours | 4.27 | 37 |
| Rechlorination | 6.51 |  |
| 24 additional hours | 5.20 | 23 |
| Rechlorination | 6.36 |  |
| 24 additional hours | 5.45 | 20 |
| Rechlorination | 6.42 |  |
| 24 additional hours | 5.52 | 19 |
| Rechlorination | 6.38 |  |

Example 6

Preparation of Unhalogenated and Chlorinated Porous Nomex/Cellulose Acetate Particles 0.1 g Nomex™ aramid fibers, which were cut into small pieces to improve dissolution, and 0.42 g LiCl were added to a flask containing 20 mL of dimethylacetamide (DMAc); the mixture was heated at 120° C. for 2 hours to complete dissolution. The solution was filtered to remove a small amount of residual undissolved material. Then 0.1 g cellulose acetate (Eastman Chemical Company, Degree of Substitution=1.7) was added to the solution, followed by heating at 50° C. for 1.5 hours.

The above solution was transferred to a syringe and injected into 200 mL of distilled water with vigorous agitation by a household blender. A uniform suspension (water, aramid, cellulose acetate, and DMAc) with some foam on the top was observed. After collapsing the foam, 20 mL of commercial household hypochlorite bleach was added to 180 mL of the above suspension so that the concentration of sodium hypochlorite was 0.6 wt % active chlorine. The chlorination was performed at room temperature for 1 hour at pH 7 which was adjusted by adding 6 M hydrochloric acid while mild stirring was applied. In order to separate aramid/cellulose acetate from the chlorination bath, the chlorinated aramid/cellulose acetate suspension was centrifuged, and the clear solvent was decanted. The precipitated porous particles were resuspended and washed in distilled water, followed by centrifugation three times. Then they were freeze dried and heated in air at 45° C. overnight to remove any residual free chlorine.

The collected particles of blended Nomex polymer/cellulose acetate were analyzed for retained chlorine using a standard iodometric/thiosulfate titration procedure. The chlorine content of the particles was 4.05 wt %.

Example 7

Preparation of Brominated Porous Nomex Particles

Nomex particles as described in Example 1 (0.15 g) were suspended in a 100 mL flask containing 50 mL of 2 N sodium hydroxide. To the stirred suspension was added dropwise bromine (0.3 g) over a period of 10 minutes. After stirring for 5 min, the pH was adjusted to 7 by the addition of 4 N acetic acid, the flask was sealed, and the mixture was stirred at room temperature for 1 hour. The brominated particles were then filtered, rinsed thoroughly with distilled water, and dried for 1 hour at 45° C. to remove any residual free bromine.

The particles were analyzed for retained bromine using a modified iodometric/thiosulfate titration procedure as in Example 1. The following equation was used to determine the weight percent Br⁺ loading on the particles:

$$Br^+ \text{ wt \%} = (N \times V \times 79.90)/(2 \times W) \times 100\%$$

where N and V are the normality (eqv/L) and volume (L), respectively, of the sodium thiosulfate consumed in the titration, and W is the weight of the sample in grams. The bromine content of the brominated particles (Nomex-Br) was measured as 4.09 wt %.

Example 8

Preparation of Unhalogenated and Chlorinated Porous Nomex/Polyurethane Particles 0.21 g Nomex™ aramid fibers, which were cut into small pieces to improve dissolution, and 0.84 g LiCl were added to a flask containing 40 mL dimethylformamide (DMF); the mixture was heated at 120° C. for 2 hours to complete dissolution. The solution was filtered to remove a small amount of residual undissolved material. Then 0.21 g polyurethane was added to the solution, followed by heating at 50° C. for 0.5 hours.

The above solution was injected into 200 mL of ethanol with vigorous agitation by a household blender. A uniform suspension (ethanol, aramid, polyurethane and DMF) was centrifuged to collect aramid/polyurethane particles which were re-suspended into water and centrifuged twice more followed by freeze drying. Aramid/polyurethane particles were chlorinated in a solution consisting of 180 mL distilled water and 20 mL commercial household hypochlorite bleach at pH 7 which was adjusted by adding 6 M hydrochloric acid. The chlorination was performed at room temperature for 1 hour while mild stirring was applied. In order to separate the chlorinated aramid/polyurethane from the chlorination bath, the chlorinated aramid/polyurethane suspension was centrifuged, and the clear solvent was decanted. The precipitated porous particles were resuspended and washed in distilled water, followed by centrifugation three times. Then they were freeze dried and heated in air at 45° C. for 1 hour to remove any residual free chlorine.

The collected particles of blended Nomex/polyurethane were analyzed for retained chlorine using a modified iodometric/thiosulfate titration procedure as in Example 1. The chlorine content of the particles was 4.17 wt %.

Throughout this application, various publications are referenced. The disclosures of these publications in their entireties are hereby incorporated by reference into this application in order to more fully describe the invention.

Various modifications and variations can be made to the compounds, compositions, and methods described herein. Other aspects of the compounds, compositions, and methods described herein will be apparent from consideration of the specification and practice of the compounds, compositions, and methods disclosed herein. It is intended that the specification and examples be considered as exemplary.

What is claimed is:

1. A composition comprising porous particles, wherein the particles comprise a meta-aramid polymer with the chemical structure

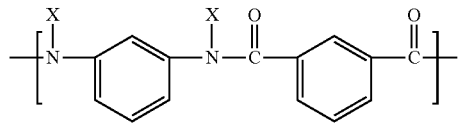

wherein the particles are prepared by dissolving meta-aramid polymer in a solvent, precipitating unhalogenated meta-aramid porous particles, and subsequently halogenating the unhalogenated meta-aramid porous particles to produce halogenated meta-aramid porous particles, wherein each X is independently H, Cl or Br, and the particles have a chlorine or bromine content from 4% to 20% by weight of the particles.

2. A composition containing the porous particles of claim 1 at a meta-aramid weight percent loading of 2 to 10 and further comprising a matrix material.

3. The composition of claim 2 wherein the matrix material is comprised of one or more of a nonwoven web, paper, textile, absorbent article, health care product, paint, filter material, powder coating, clear coating, molded plastic article, and/or binder for fibrous material.

4. The composition of claim 1 which is biocidal against microorganisms.

5. The composition of claim 1 which detoxifies chemical agents.

6. A composition comprising porous blended particles, wherein the particles are prepared by dissolving meta-aramid polymer in a solvent with one or more additional polymers, precipitating the unhalogenated blended particles comprising a mixture of meta-aramid and the additional polymer particles, and subsequently halogenating the unhalogenated meta-aramid porous particles, wherein the meta-aramid porous particles comprise a meta-aramid polymer with the structure:

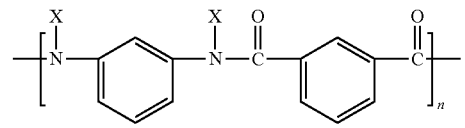

wherein each X is independently H, Cl or Br, and the particles have a chlorine or bromine content from 4% to 20% by weight of the particles.

7. The composition of claim 6 wherein the additional polymers are comprised of cellulose, cellulose acetate, polyurethane, starch, or any combination thereof.

8. A composition containing the porous blended particles of claim 6 at a meta-aramid weight percent loading of 2 to 10 and further comprising a matrix material.

9. The composition of claim 8 wherein the matrix material is comprised of one or more of a nonwoven web, paper, textile, absorbent article, health care product, paint, filter material, powder coating, a coating, molded plastic article, and/or binder for fibrous material.

10. The composition of claim 6 which is biocidal against microorganisms.

11. The composition of claim 6 which detoxifies chemical agents.

12. The composition of claim 1 wherein the solvent comprises an ionic liquid.

13. The composition of claim 12 wherein the solvent comprises 1-butyl-3-methylimidazolium chloride.

14. The composition of claim 1 wherein the solvent comprises an organic solvent.

15. The composition of claim 14 wherein the organic solvent is selected from the group consisting of formamide, dimethyl formamide, dimethyl acetamide, and tetrahydrofuran, with or without inorganic salts.

16. The composition of claim 6 wherein the solvent comprises an ionic liquid.

17. The composition of claim 16 wherein the solvent comprises 1-butyl-3-methylimidazolium chloride.

18. The composition of claim 6 wherein the solvent comprises an organic solvent.

19. The composition of claim 18 wherein the organic solvent is selected from the group consisting of formamide, dimethyl formamide, dimethyl acetamide, and tetrahydrofuran, with or without inorganic salts.

20. The composition of claim 1 wherein the unhalogenated meta-aramid porous particle is contacted with a chlorinating agent, and the chlorinating agent is selected from the group consisting of sodium hypochlorite, calcium hypochlorite, chloroisocyanurates, and dichlorohydantoins.

21. The composition of claim 6 wherein the unhalogenated meta-aramid porous particle is contacted with a chlorinating agent, and the chlorinating agent is selected from the group consisting of sodium hypochlorite, calcium hypochlorite, chloroisocyanurates, and dichlorohydantoins.

22. The composition of claim 1 wherein the unhalogenated meta-aramid porous particle is contacted with a brominating agent, and the brominating agent is selected from the group consisting of aqueous bromine, sodium or potassium hypobromite, and bromohydantoins.

23. The composition of claim 6 wherein the unhalogenated meta-aramid porous particle is contacted with a brominating agent, and the brominating agent is selected from the group consisting of aqueous bromine, sodium or potassium hypobromite, and bromohydantoins.

24. The composition of claim 1, wherein the composition comprises the porous particles suspended in a liquid.

25. The composition of claim 1, wherein the porous particles are a dry powder.

26. The composition of claim 1, wherein the particles have a chlorine content of 4% to 20% by weight of the particles.

27. The composition of claim 1, wherein the particles have a chlorine content of 5% to 20% by weight of the particles.

28. The composition of claim 1, wherein the particles have a bromine content of 4% to 20% by weight of the particles.

29. The composition of claim 1, wherein the particles have a bromine content of 5% to 20% by weight of the particles.

30. The composition of claim 6, wherein the particles have a chlorine content of 4% to 20% by weight of the particles.

31. The composition of claim 6, wherein the particles have a chlorine content of 5% to 20% by weight of the particles.

32. The composition of claim 6, wherein the particles have a bromine content of 4% to 20% by weight of the particles.

33. The composition of claim 6, wherein the particles have a bromine content of 5% to 20% by weight of the particles.

\* \* \* \* \*